US012636503B2

(12) United States Patent　　(10) Patent No.:　US 12,636,503 B2

Rock et al.　　(45) Date of Patent:　May 26, 2026

(54) ROTATABLE LEAD CONNECTORS

(71) Applicant: Medtronic, Inc., Minneapolis, MN (US)

(72) Inventors: Kaileigh E. Rock, Mahtomedi, MN (US); William J. Clemens, Fridley, MN (US); Elyssa M. Edgeton, Andover, MN (US); Thomas A. Anderson, New Hope, MN (US); Dina L. Williams, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 452 days.

(21) Appl. No.: 17/962,771

(22) Filed: Oct. 10, 2022

(65) Prior Publication Data

US 2023/0140572 A1　May 4, 2023

Related U.S. Application Data

(60) Provisional application No. 63/263,502, filed on Nov. 3, 2021.

(51) Int. Cl.
|  |  |
|---|---|
| *A61N 1/375* | (2006.01) |
| *A61N 1/05* | (2006.01) |
| *A61N 1/372* | (2006.01) |

(52) U.S. Cl.
CPC ......... *A61N 1/37241* (2013.01); *A61N 1/059* (2013.01); *A61N 1/3752* (2013.01)

(58) Field of Classification Search
None
See application file for complete search history.

(56) References Cited

U.S. PATENT DOCUMENTS

| | | | | |
|---|---|---|---|---|
| 4,577,643 A | * | 3/1986 | Beranek | A61N 1/3752 |
| | | | | 607/119 |
| 4,764,132 A | | 8/1988 | Stutz, Jr. | |
| 4,951,687 A | * | 8/1990 | Ufford | H01R 24/58 |
| | | | | 607/122 |
| 2014/0155974 A1 | * | 6/2014 | Petersen | A61N 1/059 |
| | | | | 607/119 |
| 2015/0209575 A1 | * | 7/2015 | Black | A61N 1/0558 |
| | | | | 607/116 |

(Continued)

OTHER PUBLICATIONS

PCT/IB2022/059884) PCT Notification of Transmittal of the International Search Report and the Written Opinion of the International Searching Authority, dated Feb. 22, 2023, 10 pages.

*Primary Examiner* — Erica S Lee

(74) *Attorney, Agent, or Firm* — Shumaker & Sieffert, P.A.

(57) ABSTRACT

An implantable medical lead includes a lead body, an electrode, a lead electrical connector, and a rotational electrical coupling. The lead electrical connector is configured to establish electrical communication between a test device and the electrode. The rotational electrical coupling includes a first conductive component electrically connected to the electrode and a second conductive component electrically connected to the first conductive component. The second conductive component is configured to establish electrical communication with the test device. The rotational electrical coupling is configured to facilitate rotation of the first conductive component relative to the second conductive component.

21 Claims, 5 Drawing Sheets

(56) References Cited

U.S. PATENT DOCUMENTS

| | | | |
|---|---|---|---|
| 2015/0297884 A1 | 10/2015 | Jang | |
| 2017/0361108 A1* | 12/2017 | Leven | A61N 1/3752 |
| 2020/0261725 A1 | 8/2020 | Yang et al. | |
| 2021/0178150 A1* | 6/2021 | Van Venrooij | A61N 1/375 |
| 2022/0088395 A1* | 3/2022 | Yang | A61N 1/372 |

* cited by examiner

ROTATABLE LEAD CONNECTORS

RELATED APPLICATIONS

This application claims the benefit of U.S. Provisional Application Ser. No. 63/263,502, filed Nov. 3, 2021, the entire contents of each of which are incorporated herein by reference.

TECHNICAL FIELD

This disclosure generally relates to medical devices, and more specifically, testing implantable medical leads during implantation procedures.

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads may be implanted at target locations selected to detect a physiological condition of the patient and/or deliver one or more therapies. For example, implantable medical leads may be delivered to locations within an atria or ventricle to sense intrinsic cardiac signals and deliver pacing or antitachyarrhythmia shock therapy from a medical device coupled to the lead. In other examples, implantable medical leads may be tunneled to locations adjacent a spinal cord or other nerves for delivering pain therapy from a medical device coupled to the lead. Implantable medical leads may include anchoring components to secure a distal end of the lead at the target location.

SUMMARY

In general, this disclosure is directed to devices and techniques that facilitate guiding a distal electrode fixation of an implantable medical lead, e.g., in situ or in real time, to a desired position on and/or depth within tissue, e.g., position on the endocardial surface or depth within cardiac tissue, such as the intraventricular septum, or other cardiac tissue. Electrical signals, e.g., real-time electrical signals, sensed via the distal electrode, such as pacing impedance, signals indicative of pacing capture, or electrogram signals, may be used to determine whether a current position/depth is adequate. In the case of the His-Purkinje conduction system (HPCS), for example, the presence of HPCS features (e.g., features indicative of the electrical activity of the HPCS) in the cardiac electrogram may indicate an adequate distal electrode position.

In some cases, the whole implantable medical lead or a portion thereof is rotated during the implantation procedure. However, a test device used to collect signals from the distal electrode and its associated cabling may not be configured to rotate with the lead. For example, rotation of the lead may cause the cabling of the test device to become tangled, potentially interfering with the implantation procedure.

An implantable medical lead according to this disclosure may be configured such that different portions of the implantable medical lead are rotatable relative to one another. For example, the implantable medical lead may include a rotational electrical coupling configured to allow electrical communication between the test device and an electrode of the implantable medical lead during rotation. The rotational electrical coupling may comprise a first conductive component configured to be electrically connected to the electrode, and a second conductive component configured to be electrically connected to the test device. The rotational electrical coupling is configured to facilitate rotation of the first conductive component relative to the second conductive component. In this manner, an implantable medical lead according to this disclosure may allow a test device to remain connected to a portion of the rotational electrical coupling (e.g., the second conductive component) while implanting/fixing the lead by rotating the lead body without cables associated with the test device becoming tangled. In some examples, one or both of the first and second conductive components is included as part of a lead electrical connector configured to couple the implantable medical lead to an implantable medical device (e.g., an IS-1 connector).

In some cases, rotation of the medical lead (e.g., to advance the distal electrode into tissue) may introduce artifacts or other noise into these signals used to determine whether its position/depth is adequate. For example, relative rotation of portions of a conductive path between the electrode and the test device may introduce such noise, e.g., due to make/break events occurring during the relative rotation. The noise may corrupt the signals such that the adequacy of the position/depth of the electrode cannot be determined during rotation. Consequently, the implanting physician may need to frequently stop rotating to test a position before resuming rotation, which may increase the time and effort needed for the implantation procedure.

A lead according to the present disclosure may include features to maintain an electrical connection between the first and second conductive components during rotation of the implantable medical lead and, in some examples, to reduce the presence of noise in signals sensed by the distal electrode. For example, the rotational electrical coupling may include an elastically deformable element, such as a spring, beams, or fingers, configured to maintain the second conductive component in abutment and electrical contact with the first conductive component as the medical lead moves during rotation. These features may allow an implanting physician to observe electrical signals, or data derived therefrom, during rotation of the implantable medical lead, which may reduce the time and effort needed to identify an adequate implant position/depth for the distal electrode.

In some examples, an implantable medical lead comprises: a lead body extending from a proximal portion of the implantable medical lead to a distal portion of the implantable medical lead; an electrode at the distal portion of the implantable medical lead; and a lead electrical connector at the proximal portion of the implantable medical lead, wherein the lead electrical connector is configured to establish electrical communication between a test device and the electrode; and a rotational electrical coupling, wherein at least a portion of the rotational electrical coupling is mechanically supported by the lead electrical connector, and wherein the rotational electrical coupling comprises: a first conductive component electrically connected to the electrode; and a second conductive component electrically connected to the first conductive component, wherein the second conductive component is configured to establish electrical communication with the test device, and wherein the first conductive component and the second conductive component are configured to rotate relative to each other.

In some examples, a system comprises: a medical device; a test device; an implantable medical lead electrically connected to the medical device, the implantable medical lead comprising: a lead body extending from a proximal portion of the implantable medical lead to a distal portion of the implantable medical lead; an electrode at the distal portion of the implantable medical lead; and a lead electrical connector at the proximal portion of the implantable medical lead, wherein the lead electrical connector is configured to establish electrical communication between the test device and the electrode; and a rotational electrical coupling, wherein at least a portion of the rotational electrical coupling is mechanically supported by the lead electrical connector, and wherein the rotational electrical coupling comprises: a first conductive component electrically connected to the electrode; and a second conductive component electrically connected to the first conductive component, wherein the second conductive component is configured to establish electrical communication with the test device, and wherein the first conductive component and the second conductive component are configured to rotate relative to each other.

In some examples, a method comprises: rotating, by an implantable medical lead, to advance an electrode, for implantation in patient tissue, of the implantable medical lead, wherein the implantable medical lead comprises: a lead body extending from a proximal portion of the implantable medical lead to a distal portion of the implantable medical lead; an electrode at the distal portion of the implantable medical lead; and a lead electrical connector at the proximal portion of the implantable medical lead, wherein the lead electrical connector is configured to establish electrical communication between a test device and the electrode; and a rotational electrical coupling, wherein at least a portion of the rotational electrical coupling is mechanically supported by the lead electrical connector, and wherein the rotational electrical coupling comprises: a first conductive component electrically connected to the electrode; and a second conductive component electrically connected to the first conductive component, wherein the second conductive component is configured to establish electrical communication with the test device, and first conductive component and the second conductive component are configured to rotate relative to each other; and receiving, by the test device, signals sensed via the electrode during the rotation of the implantable medical lead.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

Figure 3:
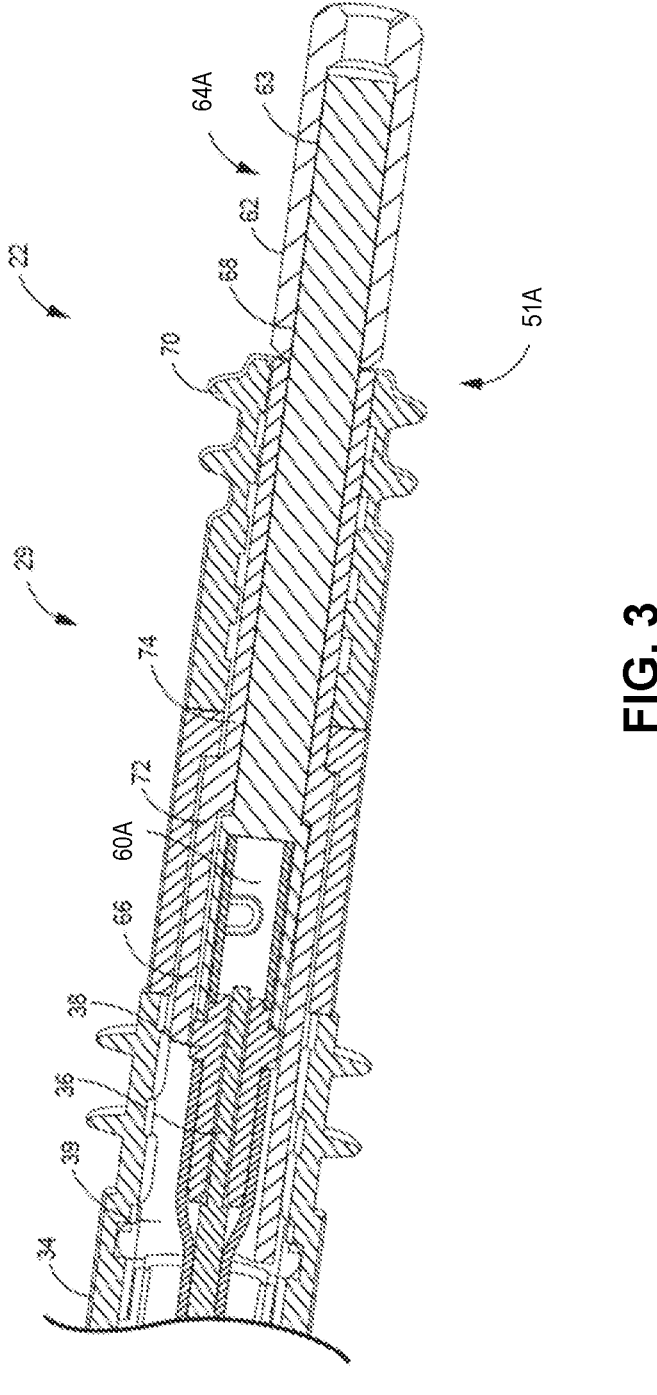

FIG. 3 is a cross-sectional diagram illustrating an example rotational electrical coupling.

Figure 4:
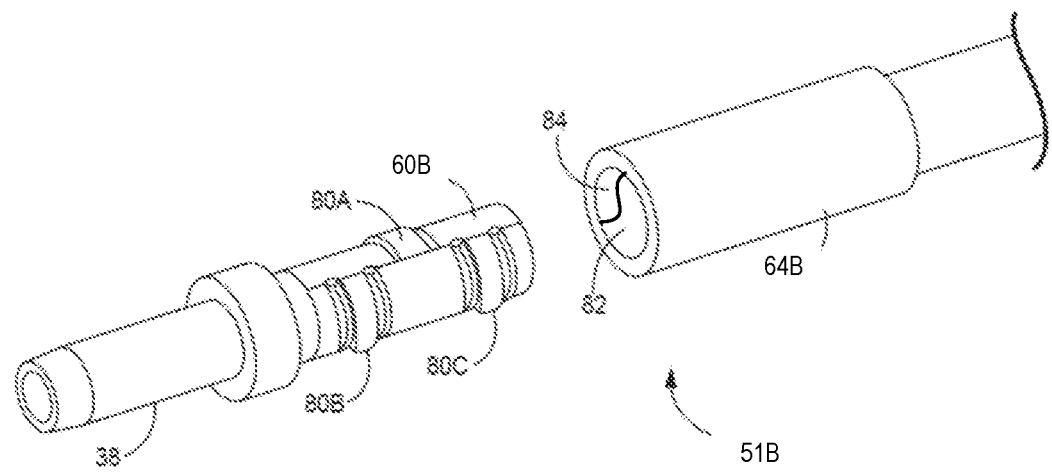

FIG. 4 is a conceptual diagram illustrating another example rotational electrical coupling.

Figure 5:
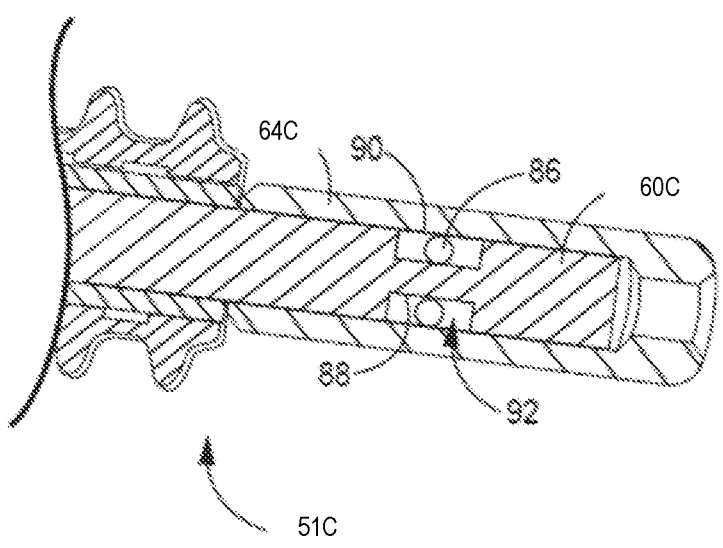

FIG. 5 is a cross-sectional diagram illustrating yet another example rotational electrical coupling.

Figure 6:
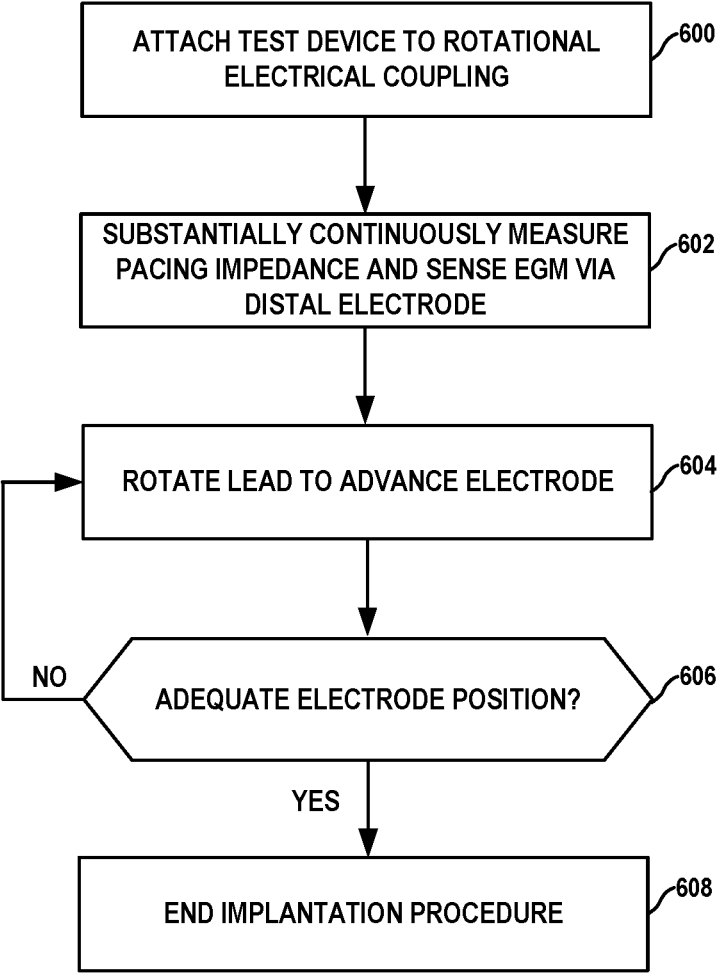

FIG. 6 is a flow diagram illustrating an example technique for testing an implantable medical lead during an implantation procedure using a rotational electrical coupling.

DETAILED DESCRIPTION

Figure 1:
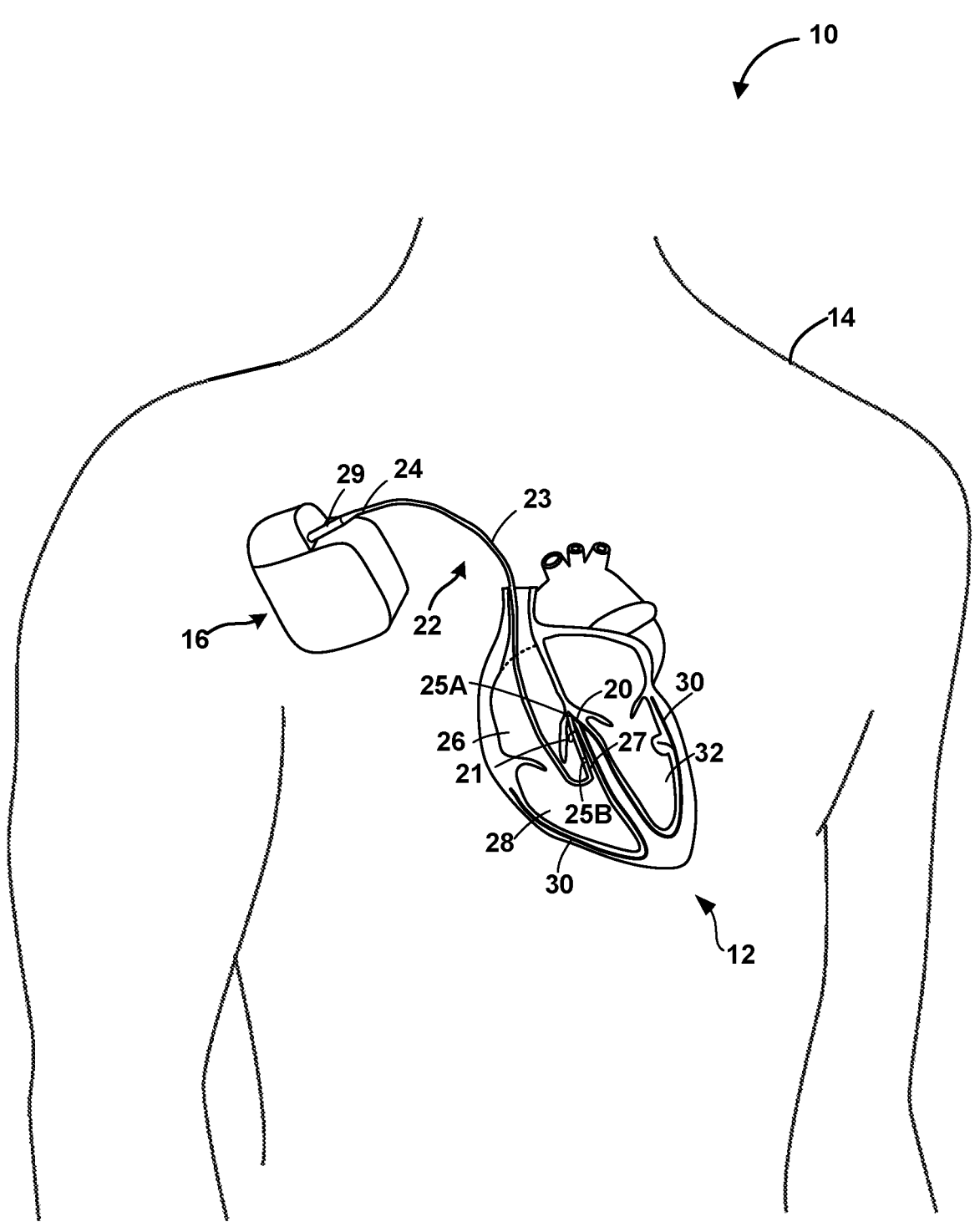
FIG. 1 is a conceptual diagram illustrating an example medical device system, including an example implantable medical lead, for delivering conduction system pacing to a patient.

FIG. 1 is a conceptual diagram illustrating an example medical device system 10 for delivering HPCS pacing to a heart 12 of a patient 14. As illustrated by example system 10 in FIG. 1, system 10 may include an implantable medical device (IMD) 16 with cardiac pacing capabilities. IMD 16 is connected to an implantable medical lead 22 ("lead 22") that includes a lead body 23 extending from a proximal portion 24 of lead 22 ("lead proximal portion 24") to a distal portion 27 of lead 22 ("lead distal portion 27"). Lead proximal portion 24 may be operably coupled to IMD 16. Although primarily described herein with respect to HPCS, the techniques of this disclosure may be applied to other regions of the heart, such as a left bundle branch (LBB) or a right bundle branch (RBB). Furthermore, although primarily described herein in the context of cardiac pacing, the techniques of this disclosure may be applied to non-cardiac contexts, such as neurostimulation.

IMD 16 senses electrical signals attendant to the depolarization and repolarization of heart 12, e.g., a cardiac EGM, via electrodes on lead 22 and/or the housing of IMD 16. IMD 16 may also deliver therapy in the form of electrical signals, e.g., cardiac pacing, to heart 12 via electrodes located on lead 22. In the illustrated example, lead 22 includes a distal electrode 25A at lead distal portion 27 and a proximal electrode 25B located proximally of distal electrode 25A (collectively, "electrodes 25"). In other examples, lead 22 may include more or fewer electrodes 25, such as examples in which lead 22 includes only electrode 25A. In some cases, lead 22 may include one or more sensors 21 at distal portion 27.

Lead 22 extends into heart 12 of patient 14 to sense electrical activity of heart 12 and/or deliver electrical stimulation to heart 12. In the example shown in FIG. 1, lead 22 extends through one or more veins (not shown), the superior vena cava (not shown), and right atrium 26, and into right ventricle 28. System 10 may include additional leads coupled to IMD 16, such as a left ventricular (LV) lead that extends through one or more veins, the vena cava, right atrium 26, and into the coronary sinus to a region adjacent to the free wall of left ventricle 32 of heart 12, and/or a lead that extends into right atrium 26.

Lead 22, e.g., distal electrode 25A, is positioned to provide pacing to the HPCS. Providing HPCS pacing is sometimes referred to as "His-Purkinje pacing." In the illustrated example, lead 22 is positioned to provide pacing to His-Purkinje 20 between an atrioventricular bundle (not shown) and branches of Purkinje fibers 30. In other examples, lead 22 and distal electrode 25A may be implanted at positions to provide pacing to other portions of the HPCS, such as the LBB or RBB.

Distal electrode 25A may be carried by a distal end of lead 22. In addition to being electrically active, distal electrode 25A may be configured to grasp tissues at or near a target site and substantially secure a distal end of lead 22 to the target site. In other words, distal electrode 25A may be configured to substantially maintain an orientation of lead 22 with respect to the target site by penetrating tissue. Distal electrode 25A may include one or more fixation tines of any shape, including, but not limited to, helically shaped fixation tines. For example, distal electrode 25A may take the form of a fixed helix, a tine tip electrode, etc.

Electrode 25B may take the form of a ring electrode electrically insulated from electrode 25A. In some examples, distal electrode 25A may be positioned within the cardiac tissue such that pacing stimulation delivered via distal electrode 25A activates the HPCS. During an implantation procedure for lead 22, an implanting physician may position a distal end of lead 22 at a desired location, and fix distal electrode 25A distally from the distal end of lead 22 to a desired depth within the cardiac tissue, e.g., the intraventricular myocardium.

Lead 22 includes a lead electrical connector 29 (sometimes referred to herein as "connector 29" or "lead connector 29"), such as an IS-1 connector, configured to establish electrical communication between IMD 16 and electrodes 25. Connector 29 is configured to electrically communicate with circuitry of IMD 16. Connector 29 includes one or more conductors (not shown) configured to electrically communicate with electrodes 25. In some examples, each of electrodes 25A and 25B is electrically coupled to a respective conductor within connector 29 and thereby coupled to circuitry within IMD 16. In examples, connector 29 is configured such that electrical communication with distal electrode 25A and proximal electrode 25B occurs substantially independently to, e.g., facilitate correct placement of electrodes 25 and/or obtain a better electrical signal (lower threshold, lower impedance, etc.).

Figure 2:
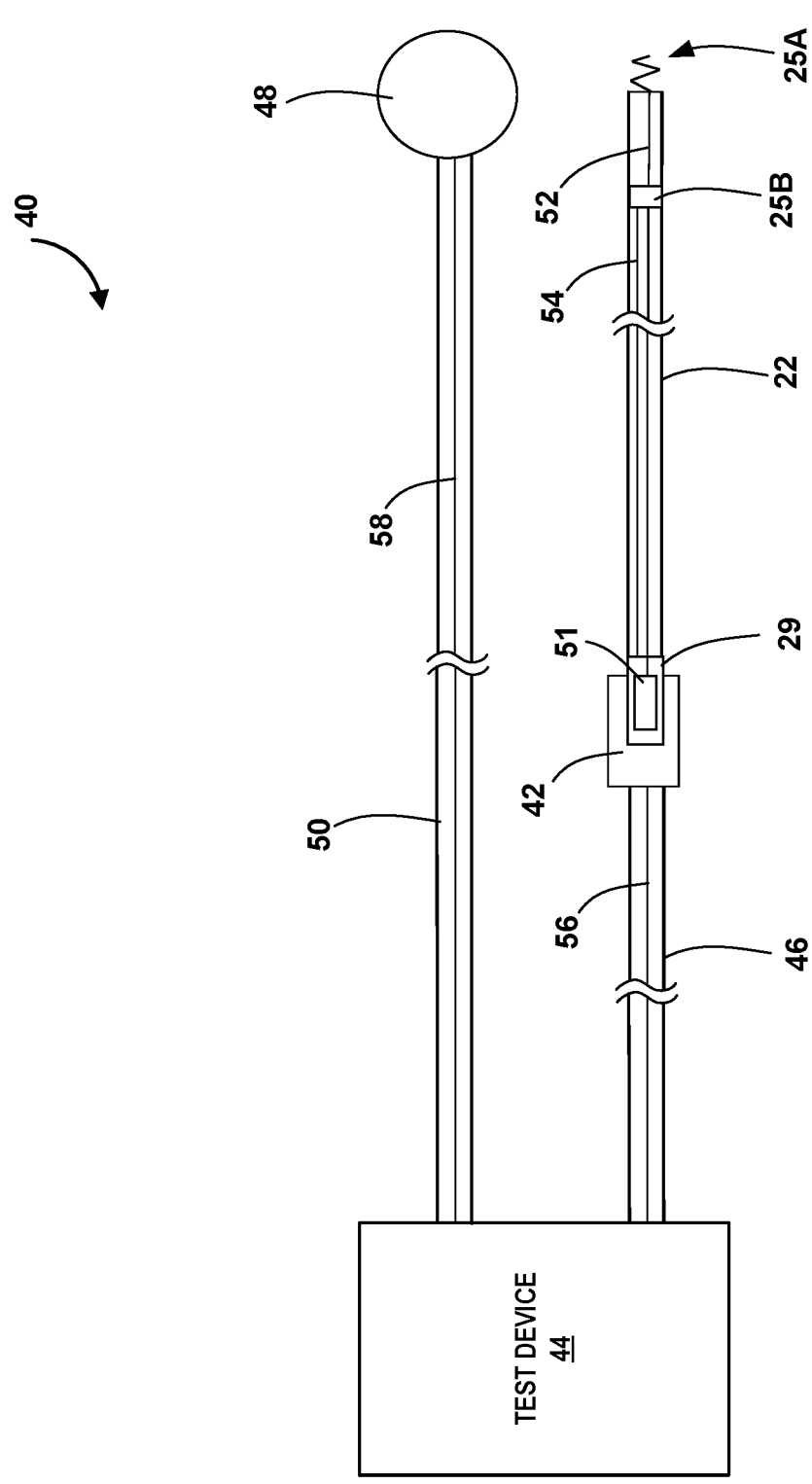
FIG. 2 is a conceptual diagram illustrating an example system for testing the implantable medical lead of FIG. 1 during an implantation procedure, the example system including a rotational electrical coupling to connect the implantable medical lead to a test device.

FIG. 2 is a conceptual diagram illustrating an example system 40 for testing lead 22 during an implantation procedure. As illustrated by the example of FIG. 2, system 40 includes a test device 44 that is connected to lead 22 via a cable 46. More particularly, cable 46 includes a distal cable connector 42, e.g., an alligator clip, configured to selectively physically and electrically connect cable 46 to lead connector 29, although other selective or permanent connections between test device 44 and lead connector 29 are possible. System 40 also includes an auxiliary electrode 48, which may be attached externally to patient 14, e.g., via an adhesive patch. Auxiliary electrode 48 may be connected to test device 44 via a cable 50.

As illustrated in FIG. 2, lead 22 includes a rotational electrical coupling 51 (sometimes referred to herein as "coupling 51"), which may be partially or wholly within lead connector 29. Rotational electrical coupling 51 is configured such that different portions of lead 22 are rotatable relative to one another, while providing an electrical connection between test device 44 and distal electrode 25A. Rotational electrical coupling 51 may comprise a first conductive component configured to be electrically connected to distal electrode 25A, and a second conductive component configured to be electrically connected to test device 44. The first conductive component and the second conductive component may be configured to rotate relative to each other.

Lead 22 may include a conductor 52 electrically connected to distal electrode 25A and a conductor 54 electrically connected to proximal electrode 25B. As will be discussed in greater detail below, conductor 52 is electrically connected to rotational electrical coupling 51. Cable 46 includes a conductor 56 which is electrically connected or connectable to both rotational electrical coupling 51 and lead connector 29 via cable connector 42, and test device 44. When lead 22, coupling 51, cable 46, and test device 44 are connected, conductors 52 and 56 electrically connect distal electrode 25A to test device 44. Auxiliary electrode 48 is also connected or connectable to test device 44 via a conductor 58 of cable 50. In the illustrated example, coupling 51 via cable 46 is configured to electrically connect one electrode of lead 22, distal electrode 25A, to test device 44 in a unipolar configuration. In other examples, coupling 51 and test device 44 may be connected to both electrodes 25 of lead 22 in a bipolar configuration, and auxiliary electrode 48 and cable 50 may be omitted.

Test device 44 receives one or more signals sensed using distal electrode 25A with auxiliary electrode 48 acting as a reference electrode. In some examples, test device 44 measures a pacing impedance signal using distal electrode 25A. In some examples, test device 44 receives a cardiac electrogram signal sensed using distal electrode 25A with auxiliary electrode 48 acting as a reference electrode. An implanting physician may use the signals and/or values derived from the signals to determine whether a current position/depth of distal electrode 25A is adequate for sensing and therapy delivery by IMD 16 via distal electrode 25A. In the case of HPCS pacing, for example, the presence of HPCS features in the cardiac electrogram (e.g., features indicative of the electrical activity of the His bundle or bundle branches) may indicate an adequate position/depth of distal electrode 25A.

In some cases, lead 22, or a portion thereof, is rotated during the implantation procedure. However, test device 44 and cables 46 and 50 may not be able to rotate with lead 22. Furthermore, rotation of lead 22 may introduce artifacts or other noise into the signals used to determine whether its position/depth is adequate. For example, relative rotation of portions of the conductive pathway may introduce such noise, e.g., due to make/break events occurring during the relative rotation. The noise may corrupt the signals such that the adequacy of the position/depth of electrode 25A cannot be determined during rotation. As described in greater detail below, rotational electrical coupling 51, e.g., including first and second conductive components, may allow relative rotation of lead 22 and cable 46, and mitigate noise associated with such rotation.

FIG. 3 is a cross-sectional diagram of an example configuration of a rotational electrical coupling 51A. In accordance with techniques of this disclosure, rotational electrical coupling 51A may facilitate rotation of lead 22 relative to test device 44 by including a portion of a conductive pathway that is rotationally fixed, like test device 44, and another portion of the conductive pathway that is rotatable with lead 22. Furthermore, rotational electrical coupling 51A may include features to mitigate noise that could otherwise be introduced into the signals received by test device 44 via electrodes 25 during rotation of lead 22.

Rotational electrical coupling 51A may be configured to establish electrical communication between distal electrode 25A and, via lead connector 29, test device 44. Lead 22 may mechanically support rotational electrical coupling 51A, and test device 44 may be in electrical contact with rotational electrical coupling 51A (e.g., via cable 46). In some cases, electrical contact between test device 44 and rotational electrical coupling 51A may be due to test device 44 being attached, fixed, or otherwise secured to rotational electrical coupling 51A or a portion of lead connector 29 electrically coupled to rotational electrical coupling 51A. As shown in FIG. 3, rotational electrical coupling 51A includes a first conductive component 60A and a second conductive component 64A.

First conductive component 60A and second conductive component 64A may be configured to rotate relative to each other. For example, first conductive component 60A, but not second conductive component 64A, may be rotationally fixed to lead body 23. In this way, lead body 23, and thus first conductive component 60A, may rotate relative to second conductive component 64A while second conductive component 64A maintains electrical communication between first conductive component 60A and test device 44.

In the illustrated example of FIG. 3, second conductive component 64A includes a pin 63 and a cap 62 that are secured to each other (e.g., crimped, welded etc.). Pin 63 may extend from a distal portion 66 to a proximal portion 68. Pin 63 may carry cap 62 and may be stationary relative (e.g., rotationally fixed) to cap 62 as first conductive component 60A rotates relative to second conductive component 64A.

Cap 62 may be electrically connected to pin 63. In examples, cap 62 and pin 63 are electrically connected by physical contact with each other, e.g., being adjacent to each other and/or physically abutted to each other. Cap 62 of second conductive component 64A may also be electrically connected to test device 44, e.g., via cable 46 and distal cable connector 42. As such, cap 62 and pin 63 may be configured to establish and maintain electrical communication between first conductive component 60A and test device 44. In some cases, cap 62 is positioned on proximal portion 68 of pin 63. In such examples, cap 62 may define a recess configured to receive proximal portion 68. IMD 16 may be electrically connected to cap 62.

First conductive component 60A is electrically connected to second conductive component 64A; in addition, first conductive component 60A is electrically connected to a connector 29. Connector 29 is configured to establish electrical communication between circuitry of IMD 16 and electrodes 25. Lead proximal portion 24 may mechanically support connector 29. Connector 29 may include a lead electrical connector body 34 ("connector body 34") configured to house at least a portion of one or more conductors (e.g., conductors 52, 54) to which electrodes 25 may be electrically connected. In examples, the one or more conductors include a conductive cable 36 ("cable 36") extending from IMD 16 and into lead electrical connector body 34. Distal portion 66 of pin 63 may be positioned within lumen 39 of connector body 34. Proximal portion 68 of pin 63 may extend beyond a proximal end 70 of connector body 34.

First conductive component 60A may include a sleeve 38 of connector 29. Sleeve 38 may be electrically connected to cable 36 and configured to electrically communicate with electrode 25A via cable 36. In examples, sleeve 38 is crimped, welded, or otherwise secured to cable 36. In turn, first conductive component 60A may be rotationally fixed to connector body 34. Sleeve 38, and at least a portion of cable 36, may be disposed within a lumen 39 defined by an inner surface of connector body 34. That is, connector body 34 may mechanically support sleeve 38.

In examples, first conductive component 60A is in abutment with second conductive component 64A to establish electrical communication without being secured (e.g., rotationally fixed) to second conductive component 64A. Thus, second conductive component 64A of rotational electrical coupling 51A may be electrically connected to electrode 25A and with circuitry of IMD 16 via first conductive component 60A. At least a portion of second conductive component 64A may be positioned proximal to first conductive component 60A. For example, cap 62 may be proximal to sleeve 38.

In examples, connector body 34 houses an electrically insulative bearing 72 ("insulative bearing 72") defining a channel configured to receive at least a portion of rotational electrical coupling 51A. Insulative bearing 72 may be formed from polyether ether ketone (PEEK) or other insulative materials. Insulative bearing 72 may be configured to facilitate rotation of at least a portion of rotational electrical coupling 51A. In examples, the channel defined by insulative bearing 72 is configured to receive distal portion 66 of pin 63. The channel may be configured to enable second conductive component 64A to substantially freely rotate within the channel. For instance, the inner surface of insulative bearing 72 defining the channel may be smooth such that any contact between insulative bearing 72 and second conductive component 64A does not substantially resist rotation of second conductive component 64A. In examples, insulative bearing 72 is bonded or otherwise secured to sleeve 38 (and, in turn, first conductive component 60A). In examples, insulative bearing 72 is bonded or otherwise secured to connector body 34.

As indicated above, rotational electrical coupling 51A may include features to mitigate noise that could otherwise be introduced into the signals received by test device 44 via distal electrode 25A during rotation of lead 22. For example, rotational electrical coupling 51A may comprise a material selected for adequate conduction and relatively lower friction, such as tin, gold, silver, or copper. In some examples, rotational electrical coupling 51A may comprise the material, e.g., be coated with the material. In some examples, rotational electrical coupling 51A may consist essentially of the material, e.g., may include other materials that do not materially affect the properties rotational electrical coupling 51A, such as properties related to electrical conduction and friction.

FIG. 4 is a conceptual diagram, illustrating an example rotational electrical coupling 51B that includes a first conductive component 60B and a second conductive component 64B. As shown in FIG. 4, first conductive component 60B defines one or more fingers 80A-80C (collectively, "fingers 80"). An inner surface 82 of second conductive component 64B, for example an inner surface of pin 63, may be configured to be in abutment with fingers 80. In some examples, inner surface 82 of second conductive component 64B may define one or more protrusions 84 configured to be in abutment with fingers 80. First conductive component 60B and second conductive component 64B may be dimensioned such that when first conductive component 60B is inserted into second conductive component 64B, first conductive component 60B and second conductive component 64B compress fingers 80 against protrusions 84 to establish electrical contact. Fingers 80 may be elastically deformable such that fingers 80 are urged into contact with inner surface 82 and/or protrusions 84.

FIG. 5 is a cross-sectional diagram of an example rotational electrical coupling 51C. As shown in FIG. 5, rotational electrical coupling 51C includes a first conductive component 60C and a second conductive component 64C. First conductive component 60C and second conductive component 64C are in electrical contact. In the illustrated example, rotational electrical coupling 51C is configured such that first conductive component 60C rotates relative to second conductive component 64C. That is, first conductive component 60C may be in abutment with, but not secured to, second conductive component 64C. In the example of FIG.

5, first conductive component 60C of rotational electrical coupling 51C may correspond to pin 63, and second conductive component 64C of rotational electrical coupling 51C may correspond to cap 62.

First conductive component 60C may be secured to connector 29. For example, first conductive component 60C may be crimped onto sleeve 38, bonded to insulative bearing 72, etc. As a result, first conductive component 60C may be configured to rotate relative to second conductive component 64C as connector body 34 (and lead body 23) rotates relative second conductive component 64C.

Rotational electrical coupling 51C may include a conductive element 86 configured to maintain first conductive component 60B in electrical communication with second conductive component 64B as first conductive component 60B rotates relative to second conductive component 64B. As shown in FIG. 5, first conductive component 60C may define a recess at a section 92 in which conductive element 86 may be positioned. In this way, conductive element 86 may be positioned between first conductive component 60C and second conductive component 64C such that conductive element 86 is in electrical contact with an outer surface 88 of first conductive component 60C and an inner surface 90 of second conductive component 64C.

In examples, conductive element 86 includes one or more ball bearings configured to be in abutment with outer surface 88 of first conductive component 60C and inner surface 90 of second conductive component 64C. The ball bearings may be formed from steel or any other suitable material (e.g., a conductive metal). The ball bearings may surround the shaft of first conductive component 60C at section 92.

In some cases, conductive element 86 includes an elastically deformable element, such as a spring, one or more beams, etc. In such cases, first conductive component 60C and second conductive component 64C may compress the elastically deformable element positioned between them to establish electrical contact. In examples where conductive element 86 is a spring, conductive element 86 may be in the shape of a ring surrounding a shaft of first conductive component 60C at section 92. The elastically deformable element may be configured to be in abutment with outer surface 88 of first conductive component 60C and inner surface 90 of second conductive component 60C. The elastically deformable element may be formed from steel or any other suitable material (e.g., a conductive metal). In examples where conductive element 86 includes one or more beams, the beams may be configured to facilitate electrical contact between first conductive component 60C and second conductive component 64C, e.g., as described in U.S. Pat. No. 4,764,132.

The likelihood of noise in the signals received by test device 44 from electrodes 25 may be reduced as the consistency of electrical and physical contact between first conductive component 60A-60C and second conductive component 64A-64C during relative rotation increases. Thus, these features, e.g., the material and geometric properties of first conductive component 60A-60C, second conductive component 64A-64C, and/or conductive element 86 may allow an implanting physician to observe relatively noise-free signals, or data derived therefrom, during rotation of lead 22, which may reduce the time and effort need to identify an adequate implant position/depth for electrodes 25.

FIG. 6 is a flow diagram illustrating an example technique for testing lead 22 during an implantation procedure using rotational electrical coupling 51A. Rotational electrical coupling 51A will be described for the example of FIG. 6, but any devices herein, or combinations of devices, may perform similar techniques of FIG. 6. According to the example of FIG. 6, test device 44 may be electrically connected to rotational electrical coupling 51A (600). In some examples, test device 44 comprises distal cable connector 42 or other connector configured to engage a portion of rotational electrical coupling 51A, such as first conductive component 60A. In this way, distal electrode 25A of lead 22 is electrically connected to test device 44 via rotational electrical coupling 51A as described herein.

Distal portion 27 of lead 22 may be positioned adjacent to cardiac tissue, e.g., the intraventricular septum, at a desired location for sensing and delivery of therapy by IMD 16, e.g., for HPCS pacing. With distal electrode 25A electrically connected to test device 44 and located as desired relative to the cardiac tissue, test device 44 may begin to measure impedance and sense a cardiac EGM via distal electrode 25A (602). Once initiated, the measurement and sensing by test device 44 may be substantially continuous, e.g., at a sampling rate during a period of time that includes a plurality of cardiac cycles and a plurality of positions/depths of distal electrode 25A. While test device 44 measures or senses one or more signals, lead 22 or a portion thereof may be rotated to advance distal electrode 25A within cardiac tissue (604). In some cases, distal electrode 25A may additionally be repositioned to different entry points of and trajectories through cardiac tissue.

Based on an output of test device 44 that is based on the one or more signals obtained via distal electrode 25A, the implanting physician may determine whether a current position/depth of distal electrode 25A is adequate for the sensing and delivery of therapy by IMD 16 (606). If the current position/depth is not adequate (NO of 606), then the physician may continue to rotate lead 22 relative to tissue of heart 12 while test device 44 continues to acquire one or more signals via distal electrode 25A. If the current position/depth is adequate (YES of 606), then the physician may end that portion of an implantation procedure for IMD 16 and lead 22 (608).

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. An implantable medical lead comprising:
a lead body comprising a first conductor extending from a proximal portion of the implantable medical lead to a distal portion of the implantable medical lead;
an electrode at the distal portion of the implantable medical lead;
a lead electrical connector at the proximal portion of the implantable medical lead, wherein the lead electrical connector is configured to establish electrical communication between a test device and the electrode; and
a rotational electrical coupling, wherein at least a portion of the rotational electrical coupling is mechanically supported by the lead electrical connector, and wherein the rotational electrical coupling comprises:
a first conductive component electrically connected to the electrode by the conductor, wherein the first conductive component is rotationally fixed to the lead body; and
a second conductive component electrically connected to the first conductive component, wherein the second conductive component is configured to establish electrical communication with the test device via a second conductor that electrically connects the second conductive component to the test device, wherein the first conductive component and the lead body are configured to rotate relative to the second conductive component, wherein the second conductive component is electrically connected to the electrode by the first conductive component, wherein the electrode is configured to be advanced by rotating the implantable medical lead including the lead body comprising the first conductor, the lead electrical connector, and the electrode, and wherein the rotational electrical coupling is configured to allow the implantable medical lead to rotate relative to the second conductor that electrically connects the second conductive component to the test device.

2. The implantable medical lead of claim 1, wherein the first conductive component comprises a sleeve, and wherein the second conductive component comprises a pin and a cap.

3. The implantable medical lead of claim 2, wherein a proximal portion of the pin is configured to be positioned within a recess defined by the cap, and wherein the pin is rotationally fixed to the cap.

4. The implantable medical lead of claim 1, wherein a distal portion of the second conductive component is configured to be positioned within the lead electrical connector.

5. The implantable medical lead of claim 1, wherein the first conductive component defines one or more fingers, and wherein an inner surface of the second conductive component is configured to be in abutment with the one or more fingers.

6. The implantable medical lead of claim 5, wherein the inner surface of the second conductive component defines one or more protrusions, and wherein the one or more protrusions are configured to be in abutment with the one or more fingers.

7. The implantable medical lead of claim 1, wherein the first conductive component comprises a pin, and wherein the second conductive component comprises a cap.

8. The implantable medical lead of claim 7, wherein the rotational electrical coupling comprises a conductive element configured to maintain the first conductive component in electrical contact with the second conductive component as the first conductive component rotates relative to the second conductive component.

9. The implantable medical lead of claim 8, wherein the conductive element comprises one or more ball bearings configured to be in abutment with an outer surface of the first conductive component and an inner surface of the second conductive component.

10. The implantable medical lead of claim 8, wherein the conductive element comprises a spring ring configured to be in abutment with an outer surface of the first conductive component and an inner surface of the second conductive component.

11. The implantable medical lead of claim 1, wherein the first conductive component is secured to an insulative bearing of the implantable medical lead such that the first conductive component is configured to rotate relative to the second conductive component as the lead body rotates relative to the second conductive component.

12. A method comprising:
rotating, by an implantable medical lead, to advance an electrode, for implantation in patient tissue, of the implantable medical lead, wherein the implantable medical lead comprises:
a lead body comprising a first conductor extending from a proximal portion of the implantable medical lead to a distal portion of the implantable medical lead;
an electrode at the distal portion of the implantable medical lead;
a lead electrical connector at the proximal portion of the implantable medical lead, wherein the lead electrical connector is configured to establish electrical communication between a test device and the electrode; and
a rotational electrical coupling, wherein at least a portion of the rotational electrical coupling is mechanically supported by the lead electrical connector, and wherein the rotational electrical coupling comprises:
a first conductive component electrically connected to the electrode by the first conductor, wherein the first conductive component is rotationally fixed to the lead body; and
a second conductive component electrically connected to the first conductive component, wherein the second conductive component is configured to establish electrical communication with the test device via a second conductor that electrically connects the second conductive component to the test device, wherein the first conductive component and the lead body are configured to rotate relative to the second conductive component, wherein the second conductive component is electrically connected to the electrode by the first conductive component, wherein the electrode is configured to be advanced by rotating the implantable medical lead including the lead body comprising the first conductor, the lead electrical connector, and the electrode, and wherein the rotational electrical coupling is configured to allow the implantable medical lead to rotate relative to the second conductor that electrically connects the second conductive component to the test device; and receiving, by the test device, signals sensed via the electrode during the rotation of the implantable medical lead.

13. The method of claim 12, wherein the first conductive component comprises a sleeve, and wherein the second conductive component comprises a pin and a cap, wherein a proximal portion of the pin is configured to be positioned within a recess defined by the cap, and wherein the pin is rotationally fixed to the cap.

14. The method of claim 12, wherein the first conductive component defines one or more fingers, and wherein an inner surface of the second conductive component is configured to be in abutment with the one or more fingers.

15. The method of claim 14, wherein the inner surface of the second conductive component defines one or more protrusions, and wherein the one or more protrusions are configured to be in abutment with the one or more fingers.

16. The method of claim 12, wherein the first conductive component comprises a pin, and wherein the second conductive component comprises a cap, wherein the rotational electrical coupling comprises a conductive element configured to maintain the first conductive component in electrical contact with the second conductive component as the first conductive component rotates relative to the second conductive component while rotating to advance the electrode.

17. The method of claim 12, wherein the first conductive component is secured to an insulative bearing of the implantable medical lead such that the first conductive component is configured to rotate relative to the second conductive component while rotating to advance the electrode.

18. The method of claim 12, wherein the electrode comprises a fixed helix configured to grasp tissues at or near a target site during rotation of the lead body.

19. The method of claim 12, wherein the signals sensed via the electrode during the rotation of the implantable medical lead comprise a cardiac electrogram signal in which His-Purkinje conduction system features can be detected.

20. The method of claim 12, wherein the signals sensed via the electrode during the rotation of the implantable medical lead comprise a cardiac electrogram signal in which left bundle branch tissue features can be detected.

21. A system comprising:

a test device;

an implantable medical lead electrically connected to the test device, the implantable medical lead comprising:

a lead body comprising a first conductor extending from a proximal portion of the implantable medical lead to a distal portion of the implantable medical lead;

an electrode at the distal portion of the implantable medical lead;

a lead electrical connector at the proximal portion of the implantable medical lead, wherein the lead electrical connector is configured to establish electrical communication between the test device and the electrode; and a rotational electrical coupling, wherein at least a portion of the rotational electrical coupling is mechanically supported by the lead electrical connector, and wherein the rotational electrical coupling comprises:

a first conductive component electrically connected to the electrode by the first conductor, wherein the first conductive component is rotationally fixed to the lead body; and a second conductive component electrically connected to the first conductive component, wherein the second conductive component is configured to establish electrical communication with the test device via a second conductor that electrically connects the second conductive component to the test device, wherein the first conductive component and the lead body are configured to rotate relative to the second conductive component, wherein the second conductive component is electrically connected to the electrode by the first conductive component, wherein the electrode is configured to be advanced by rotating the implantable medical lead including the lead body comprising the first conductor, the lead electrical connector, and the electrode, and wherein the rotational electrical coupling is configured to allow the implantable medical lead to rotate relative to the second conductor that electrically connects the second conductive component to the test device.

* * * * *